United States Patent
Egberg et al.

(10) Patent No.: US 10,201,612 B2
(45) Date of Patent: Feb. 12, 2019

(54) DEVICES AND METHODS FOR CONTROLLING HEADSPACE HUMIDITY AND OXYGEN LEVELS

(71) Applicant: Boveda, Inc., Minnetonka, MN (US)

(72) Inventors: David C. Egberg, Bonita Springs, FL (US); Robert L. Esse, Monticello, MN (US)

(73) Assignee: Boveda, Inc., Minnetonka, MN (US)

( * ) Notice: Subject to any disclaimer, the term of this patent is extended or adjusted under 35 U.S.C. 154(b) by 0 days.

(21) Appl. No.: 15/695,297

(22) Filed: Sep. 5, 2017

(65) Prior Publication Data

US 2017/0360936 A1     Dec. 21, 2017

Related U.S. Application Data

(63) Continuation of application No. 14/854,159, filed on Sep. 15, 2015, now Pat. No. 9,750,811.

(51) Int. Cl.

| | |
|---|---|
| *A61L 9/00* | (2006.01) |
| *A61K 47/22* | (2006.01) |
| *A23L 3/3436* | (2006.01) |
| *A61K 47/12* | (2006.01) |
| *B01J 20/22* | (2006.01) |
| *B01D 53/14* | (2006.01) |

(Continued)

(52) U.S. Cl.
CPC .......... *A61K 47/22* (2013.01); *A23L 3/3436* (2013.01); *A23L 3/3517* (2013.01); *A23L 3/3544* (2013.01); *A61K 47/12* (2013.01); *B01D 53/14* (2013.01); *B01D 53/1493* (2013.01); *B01J 20/22* (2013.01); *B01J 20/2805* (2013.01); *B65D 81/268* (2013.01); *A23V 2002/00* (2013.01); *B01D 2251/80* (2013.01); *B01D 2252/103* (2013.01); *B01D 2252/60* (2013.01); *B01D 2257/104* (2013.01); *B01D 2257/80* (2013.01)

(58) Field of Classification Search
CPC .. A61L 2/00; A01N 25/18; A23L 3/00; B65D 81/28
USPC ...................................... 422/1, 28, 305–306
See application file for complete search history.

(56) References Cited

U.S. PATENT DOCUMENTS

| | | |
|---|---|---|
| 339,492 A | 4/1886 | Levi |
| 1,241,695 A | 4/1917 | Moyer |

(Continued)

FOREIGN PATENT DOCUMENTS

| | | |
|---|---|---|
| CH | 667514 | 10/1988 |
| CN | 101128891 | 2/2008 |

(Continued)

OTHER PUBLICATIONS

Ageless® Oxygen Absorber Instruction Manual, Mitsubishi Gas Chemical Company, Inc., May 2011 (32 pages).

(Continued)

*Primary Examiner* — Monzer R Chorbaji
(74) *Attorney, Agent, or Firm* — Padmanabhan & Dawson PLLC.

(57) ABSTRACT

A humidity control device for use in maintaining the desired humidity of a closed environment, e.g., a container, while also decreasing headspace oxygen, the device including a water vapor and oxygen permeable pouch, an aqueous salt solution containing humidity controlling salts in combination with salts of ascorbic acid or isomers thereof.

20 Claims, 1 Drawing Sheet

(51) Int. Cl.
  *B65D 81/26* (2006.01)
  *B01J 20/28* (2006.01)
  *A23L 3/3517* (2006.01)
  *A23L 3/3544* (2006.01)

(56) References Cited

U.S. PATENT DOCUMENTS

| | | | |
|---|---|---|---|
| 1,268,135 A | 6/1918 | McElroy |
| 1,425,790 A | 8/1922 | Moyer |
| 1,481,971 A | 1/1924 | Whiting |
| 1,556,951 A | 10/1925 | Marshall |
| 1,841,889 A | 1/1932 | Grunwald |
| 1,866,560 A | 7/1932 | Gordon et al. |
| 1,871,418 A | 8/1932 | McKee |
| 1,871,419 A | 8/1932 | McKee |
| 1,967,554 A | 7/1934 | Gross et al. |
| 1,972,118 A | 9/1934 | McDill |
| 1,998,683 A | 4/1935 | Montgomery |
| 2,085,600 A | 6/1937 | Petersen |
| 2,169,055 A | 8/1939 | Overshiner |
| 2,227,158 A | 12/1940 | Saul |
| 2,236,024 A | 3/1941 | Tyler |
| 2,270,603 A | 1/1942 | Ridder |
| 2,329,908 A | 9/1943 | Johnson |
| 2,365,185 A | 12/1944 | Gailey |
| 2,368,140 A | 1/1945 | Johnson |
| 2,452,957 A | 11/1948 | Sabin |
| 2,458,695 A | 1/1949 | Edelston |
| 2,545,710 A | 3/1951 | Snyder |
| 2,758,932 A | 8/1956 | Scott |
| 2,807,514 A | 9/1957 | Williams |
| 3,135,566 A | 6/1964 | Charles |
| 3,204,388 A | 9/1965 | Asker |
| 3,211,503 A | 10/1965 | Barnes |
| 3,254,784 A | 6/1966 | Lancesseur |
| 3,315,447 A | 4/1967 | Meier |
| 3,578,545 A | 5/1971 | Carlson et al. |
| 3,719,033 A | 3/1973 | Den Boer |
| 3,722,188 A | 3/1973 | Cullen |
| 3,785,556 A | 1/1974 | Watkins |
| 3,801,011 A | 4/1974 | Guehler et al. |
| 3,815,828 A | 6/1974 | Engel |
| 3,820,309 A | 6/1974 | Cullen et al. |
| 3,897,226 A | 7/1975 | Doherty |
| 3,990,872 A | 11/1976 | Cullen |
| 4,027,068 A | 5/1977 | Saad |
| 4,127,503 A | 11/1978 | Yoshikawa et al. |
| 4,145,001 A | 3/1979 | Weyenberg et al. |
| 4,146,277 A | 3/1979 | Santoro |
| 4,150,372 A | 4/1979 | Foote |
| 4,158,440 A | 6/1979 | Sullivan et al. |
| 4,161,283 A | 7/1979 | Hyman |
| 4,192,773 A | 3/1980 | Yoshikawa et al. |
| 4,223,070 A | 9/1980 | Hahn et al. |
| 4,279,350 A | 7/1981 | King |
| 4,285,468 A | 8/1981 | Hyman |
| 4,287,995 A | 9/1981 | Moriya |
| 4,384,972 A | 5/1983 | Nakamura et al. |
| 4,406,843 A | 9/1983 | Nakamura et al. |
| 4,423,080 A | 12/1983 | Bedrosian |
| 4,445,641 A | 5/1984 | Baker et al. |
| 4,524,015 A | 6/1985 | Takahashi et al. |
| 4,528,228 A | 7/1985 | Clevenger |
| 4,572,051 A | 2/1986 | Laskin |
| 4,594,082 A | 6/1986 | Catherwood, Sr. |
| 4,614,528 A | 9/1986 | Lennen |
| 4,615,923 A | 10/1986 | Marx |
| 4,645,698 A | 2/1987 | Matsubara |
| 4,649,793 A | 3/1987 | Blackshear et al. |
| 4,686,776 A | 8/1987 | Matsubara |
| RE32,513 E | 10/1987 | Seaber et al. |
| 4,749,392 A | 6/1988 | Aoki et al. |
| 4,756,726 A | 7/1988 | Peace |
| 4,772,300 A | 9/1988 | Cullen et al. |
| 4,783,206 A | 11/1988 | Cullen et al. |
| 4,822,500 A | 4/1989 | Dobson, Jr. et al. |
| 4,834,234 A | 5/1989 | Sacherer et al. |
| 4,891,141 A | 1/1990 | Christensen et al. |
| 4,934,524 A | 6/1990 | St. Charles |
| 5,035,731 A | 7/1991 | Spruill et al. |
| 5,037,459 A | 8/1991 | Spruill et al. |
| 5,114,003 A | 5/1992 | Jackisch et al. |
| 5,130,018 A | 7/1992 | Tolman et al. |
| 5,219,075 A | 6/1993 | White |
| 5,284,871 A | 2/1994 | Graf |
| 5,289,751 A | 3/1994 | Light |
| 5,641,425 A | 6/1997 | McKedy et al. |
| 5,773,105 A | 6/1998 | Klett |
| 5,846,450 A | 12/1998 | Atkinson |
| 5,885,481 A | 3/1999 | Venkateshwaran et al. |
| 5,934,773 A | 8/1999 | Ferrell |
| 5,936,178 A | 8/1999 | Saari |
| 5,977,212 A | 11/1999 | Ebner et al. |
| 6,139,935 A | 10/2000 | Cullen et al. |
| 6,158,580 A | 12/2000 | Davis |
| 6,244,432 B1 | 6/2001 | Saari et al. |
| 6,274,209 B1 | 8/2001 | Pagidas et al. |
| 6,436,872 B2 | 8/2002 | McKedy |
| 6,508,955 B1 | 1/2003 | DelDuca et al. |
| 6,514,321 B1 | 2/2003 | Lehto et al. |
| 6,571,942 B2 | 6/2003 | Riemenschneider et al. |
| 6,620,992 B1 | 9/2003 | Kinnaird |
| 6,646,121 B2 | 11/2003 | El Kabbani et al. |
| 6,666,988 B2 | 12/2003 | DelDuca et al. |
| 6,921,026 B2 | 7/2005 | Saari et al. |
| 6,926,846 B1 | 8/2005 | DelDuca et al. |
| 6,986,807 B2 | 1/2006 | Brunk |
| 7,147,799 B2 | 12/2006 | DelDuca et al. |
| 7,475,773 B2 | 1/2009 | Lancesseur et al. |
| 8,048,201 B2 | 11/2011 | Dukes et al. |
| 8,087,645 B2 | 1/2012 | Hepple |
| 8,220,782 B2 | 7/2012 | Hepple |
| 8,590,719 B2 | 11/2013 | Sprishen et al. |
| 8,748,723 B1 | 6/2014 | Egberg et al. |
| 9,750,811 B2 | 9/2017 | Egberg et al. |
| 2003/0203081 A1 | 10/2003 | Saari et al. |
| 2004/0022676 A1* | 2/2004 | Hamilton ............... A61L 2/20 422/37 |
| 2004/0045969 A1 | 3/2004 | Chiang |
| 2004/0198611 A1 | 10/2004 | Atkinson et al. |
| 2004/0224144 A1 | 11/2004 | Saari et al. |
| 2006/0097223 A1 | 5/2006 | Powers et al. |
| 2007/0014686 A1 | 1/2007 | Arnold et al. |
| 2007/0114140 A1 | 5/2007 | Portier |
| 2008/0314772 A1 | 12/2008 | Saari et al. |
| 2010/0304357 A1 | 12/2010 | Meyers et al. |
| 2011/0017615 A1 | 1/2011 | Logel et al. |
| 2011/0079525 A1 | 4/2011 | Peck et al. |
| 2011/0221393 A1 | 9/2011 | Lim et al. |
| 2012/0020833 A1 | 1/2012 | Cook et al. |
| 2013/0334074 A1 | 12/2013 | Wada |
| 2014/0209488 A1 | 7/2014 | Dai |
| 2014/0270581 A1 | 9/2014 | Jons |
| 2014/0339106 A1 | 11/2014 | Schanin et al. |
| 2015/0053579 A1 | 2/2015 | Lebon et al. |
| 2015/0136618 A1 | 5/2015 | Patel et al. |
| 2015/0259115 A1 | 9/2015 | Yeh |
| 2015/0328584 A1 | 11/2015 | Egberg et al. |
| 2016/0031627 A1 | 2/2016 | Yeh |

FOREIGN PATENT DOCUMENTS

| | | |
|---|---|---|
| EP | 0212913 | 3/1987 |
| EP | 317041 | 5/1989 |
| EP | 348840 | 1/1990 |
| EP | 363194 | 11/1990 |
| EP | 0531075 | 3/1993 |
| EP | 0657277 | 6/1995 |
| EP | 0866111 | 9/1998 |
| FR | 1246918 | 10/1960 |
| FR | 2620685 | 3/1989 |
| GB | 2222816 | 3/1990 |

(56) References Cited

FOREIGN PATENT DOCUMENTS

| WO | 9857321 | 12/1998 |
|---|---|---|
| WO | 03065821 | 8/2003 |

OTHER PUBLICATIONS

Ageless® Product Page, Mitsubishi Gas Chemical America, copyright 2015. Accessed on the Internet Aug. 10, 2015 URL:<http://ageless.mgc-a.com/product/ageless> (2 pages).
Deutsch, JC "Ascorbic acid oxidation by hydrogen peroxide", Anal Biochem, Jan. 1, 1998, 255(1): 1-7. Abstract only (1 page).
FreshPax® Oxygen Absorber Product Page, Multisorb Technologies, copyright 2015. Accessed on the Internet Aug. 10, 2015 URL:<http://www.multisorb.com/products-and-systems/freshpax-oygen-absorber-packets-and-strips> (6 pages).
International Search Report and Written Opinion for related PCT Application No. PCT/US2016/021496 dated Jun. 15, 2016 (10 pages).
StayFresh® SF5CS1500EE-500cc Oxygen Absorbers Product Page, Impak Corporation, copyright 2014. Accessed on the Internet Aug. 10, 2015 URL:<http://www.impakcorporation.com/oxygen_absorbers/SF5CS1500EE> (2 pages).
International Search Report and Written Opinion for related PCT Application PCT/US2017/056394 dated Jan. 9, 2018 (15 pages).
International Search Report and Written Opinion for related PCT Application PCT/US2017/056341 dated Feb. 7, 2018 (11 pages).
International Search Report and Written Opinion for related PCT Application No. PCT/US2014/015547 dated May 26, 2014 (10 pages).
International Search Report for related PCT Application No. PCT/US98/11968 dated Sep. 15, 1998 (1 page).
Credo of Marseille, France: "the Tube"; Humidity Regulator for Pocket Humidor. Cited with respect to U.S. Pat. No. 5,936,178; Dec. 22, 1997 (6 pages).
Western Humidor Corporation of USA; "Torpedo"; Humifier Portable Humidification System,. Cited with respect to U.S. Pat. No. 5,936,178; Dec. 22, 1997 (6 pages).
PTCA Industries, Inc., P.O. Box 16360 (Office), San Francisco, CA 94116; P.O. Box 250 (Factory), San Carlos, CA 94070; Phone (415) 592 7311; "Humatic 50"; Conditions and maintains up to 50 cigars; U.S. and foreign patents pending. Cited with respect to U.S. Pat. No. 5,936,178; Dec. 22, 1997 (6 pages).
Caribbean Cigar Company or Miami, Florida; "Simple 70 Solution & Humidification"; The Humidification Solution. Cited with respect to U.S. Pat. No. 5,936,178; Dec. 22, 1997 (6 pages).
Owner unknown; "DHS"; Disposable Humidifcation System. Cited with respect to U.S. Pat. No. 5,936,178; Dec. 22, 1997 (6 pages).
Altura Company, Division of Peak Innovations, Inc. Quality Preserved, 6159 Omni Park Drive, Suite B, Mobile, AL 36609; Phone (334) 639-0345; Fax (334) 639-8983; e-mail: peak@mobls.com; "Humi-Pouch"; "Humi-Ship"; "Humi-Box"; patent pending. Cited with respect to U.S. Pat. No. 5,936,178; Dec. 22, 1997 (6 pages).
Mechanical and Electrical Products Rust-Proof, Packaging Handbook, Zhang KF et al. Aviation Industry Press, Oct. 31, 1990. https://vpn.hw.sipo/proxy-99148242/n/print.jsp (8 pages).

* cited by examiner

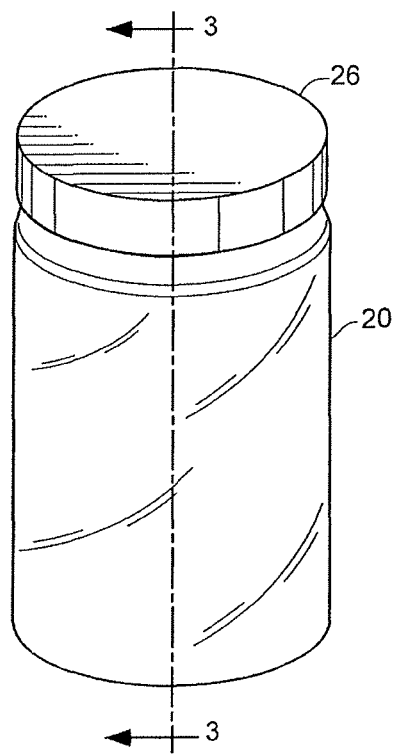
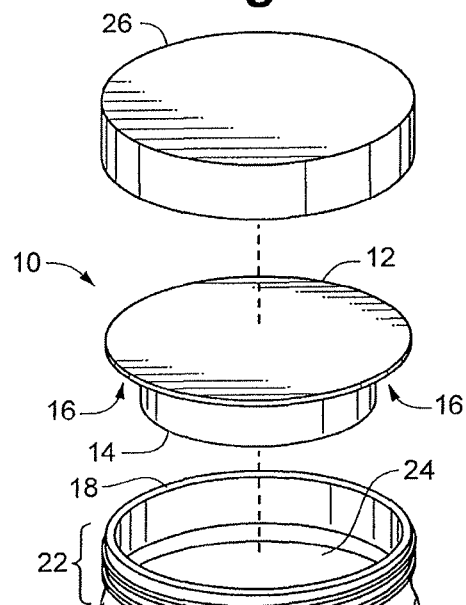
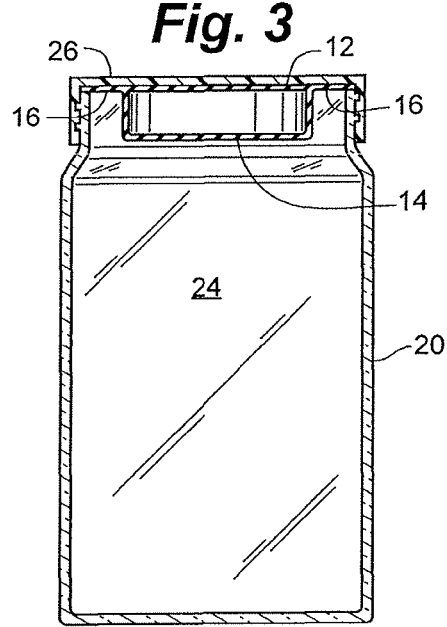

DEVICES AND METHODS FOR CONTROLLING HEADSPACE HUMIDITY AND OXYGEN LEVELS

CROSS-REFERENCE TO RELATED APPLICATIONS

None

STATEMENT REGARDING FEDERALLY SPONSORED RESEARCH OR DEVELOPMENT

Not Applicable

BACKGROUND OF THE INVENTION

Field of the Invention

The disclosure relates to generally to devices and methods for the preservation of substances and object that are sensitive to oxygen and humidity. More specifically, certain foods, pharmaceuticals, botanicals and herbs may benefit.

Description of the Related Art

Many foods and botanicals or herbs, such as cannabis, are most stable and best consumed at a certain water activity. These substances are also subject to degradation due to the chemical reaction of certain components with oxygen found in the surrounding atmosphere frequently called headspace. For example, the unsaturated lipids in food products and the terpenes in cannabis readily react with molecular oxygen to form undesirable oxidation products, thus degrading the quality and even the efficacy of the food or botanical.

As disclosed in U.S. Pat. No. 5,936,178, the relative humidity of closed environments can be stabilized by the use of humidity control systems comprised of moisture permeable pouches containing specific salt solutions. Also, certain non-ionic solutions containing low molecular weight molecules such as ethylene glycol, propylene glycol, glycerin, urea, guanidine, ethanol amine, simple sugars, or sugar alcohols may be employed. The choice of the solute and the solute concentration in an aqueous solution determines the solution water activity (aw). A solution of a certain water activity will equilibrate with the surrounding atmosphere until the relative humidity (RH) is equivalent to the water activity multiplied by 100. That is, the RH percentage will equal the water activity×100. For example, an aqueous solution of saturated sodium chloride with excess crystals, aw 0.75 will equilibrate with the moist air or dry air in a closed system until a relative humidity of 75 percent is achieved.

The moisture transfer capacity (MTC) is defined as the amount of moisture transferred, into or out of, a given control system, i.e. device, pouch, etc., over a defined relative humidity range. For example, a saturated solution of sodium chloride can transfer about 65% moisture, maintaining a water activity of 0.75. Clearly an aqueous system would be required to have sufficient MTC to maintain the RH of certain products.

The choice of salt solution is not only important because of its ability to define the relative humidity, the salt must not chemically degrade the pouch film construction or emit, outgas, corrosive or obnoxious substances.

A number of dry oxygen absorbing packets are currently marketed. These include brand names like AGELESS®, StayFresh® and FreshPax®. The technology is based on the chemical reaction of oxygen with a metal, typically iron. U.S. Pat. No. 4,127,503 describes this technology and is incorporated herein in its entirety by reference. More recently, U.S. Pat. No. 8,048,201, also incorporated herein in its entirety by reference, discloses a system comprised of a wicking agent, malic acid and iron at pH 2 to 3. The wicking agent absorbs atmospheric water and activates the acid which reacts with iron to consume oxygen. These systems are very efficient and are commonly employed to decrease headspace oxygen in a variety of applications. These systems, however, are not dual action humidity and oxygen control. These oxygen scavenger systems are packaged in films that are readily permeable to oxygen, but not necessarily suitable to fulfill the dual function of humidity control and oxygen elimination disclosed in this patent.

Further, in U.S. Pat. No. 6,921,026, commonly owned by the current assignee Boveda, Inc., Saari discloses a method for the dual control of headspace humidity and oxygen comprised of an aqueous salt solution and elemental iron. U.S. Pat. No. 6,921,026 is incorporated by reference herein in its entirety. While this method controls humidity, the rate of oxygen reaction with the metal is too slow to be of commercial value and, therefore, is susceptible to improvement. Ascorbic acid salts chemically react with molecular oxygen to form hydrogen peroxide and dehydroascorbic acid salts. The hydrogen peroxide is consumed by further reacting with ascorbic acid, dehydroascorbic acid salts to form tetahydroxydiketohexanoic acid salts. See Deutsch, J C, Anal. Biochem, 1998 Jan. 1; 255(1):1-7, also incorporated herein in its entirety by reference. Clearly isomers of ascorbic acid such as erythorbic acid salts will behave in a similar fashion.

While this ascorbate oxidation reaction has been employed to remove dissolved oxygen from boiler water as taught by U.S. Pat. No. 4,891,141, incorporated herein in its entirety by reference, the use of this reaction mixed with inorganic salts to decrease headspace oxygen has not been reported. Furthermore, it was discovered that metallic iron in conjunction with the ascorbate salt increased the rate of oxygen headspace removal.

Accordingly, there exists a need for an improved method to control headspace humidity and oxygen by combining certain salt solutions with ascorbic acid salts or isomers thereof alone or in combination with iron between pH 6 and 10.

BRIEF SUMMARY OF THE INVENTION

The present invention provides devices in the form of packets or pouches containing liquid systems in the form of humidity and oxygen control solutions for controlling the relative humidity and oxygen in a generally closed environment, e.g., an enclosure comprising a closure mechanism such as a lidded container. This invention discloses preferred systems providing superior moisture transfer capacity for stabilizing the relative humidity and oxygen. The disclosed formulas provide superior moisture transfer capacity without undo outgas, or package degradation. In a preferred form, the present invention employs a saturated aqueous solution in combination with ascorbate salts or isomers such as erythorbate. These solutions may be contained in certain polymeric films that will allow the transfer of moisture vapor and oxygen without transfer of the liquid solution.

Certain thickening agents may be added to these solutions in order to increase the viscosity. A high viscosity product will minimize undesirable solution leakage in the event of a package defect as well as affect the nature of crystal formation. Many potential thickening agents were disclosed in U.S. Pat. No. 5,936,178 discussed supra. In the present invention, the preferred thickening agents include hydroxyethylcellulose (Natrosol®) and xanthan gum.

The various embodiments of the humidity and oxygen control solution disclosed herein in accordance with this invention are introduced into pouches formed at least partly from polymeric films that breathe in a manner such that they will transport moisture vapor and oxygen but will contain the solution without leaking liquid. The water vapor transport, known as water vapor transmission rate (WVTR) is measured in terms of grams of water passed per 100 square inches of material per 24 hours under standard test conditions. It is a function of the type of film used and the thickness of the film. The total moisture transferred, of course, is also determined by the area of film exposed to a humidity control solution in a given application. It has been shown that a WVTR of about 60 grams water per 100 square inches over 24 hours provides good results for a device in accordance with the invention. Packaging film materials that may be employed include fibrous polyethylene (TYVEK®), polyesters such as the elastomer Hytrel®, or polyamide Pebax laminated onto a suitable substrate such as paper.

However, the relative humidity control device is not limited to a polymeric film pouch. Any container or material that will transport water vapor while retaining the liquid can provide a suitable container for the humidity control solutions of the invention. The thermal formed bottle lid shown in FIG. 1 is an example of a container which, when formed from Hytrel or suitable alternative, will control the oxygen and humidity in an essentially closed container.

BRIEF DESCRIPTION OF THE SEVERAL VIEWS OF THE DRAWINGS

FIG. 1 illustrates a perspective view of one embodiment of the present invention;
FIG. 2 illustrates a perspective view of one embodiment of the present invention; and
FIG. 3 illustrates a side cutaway view of one embodiment of the prevent invention.

DETAILED DESCRIPTION OF THE INVENTION

The following describes one or more embodiments of the present invention in detail offered by way of example and is not meant to limit the scope of the invention as other combinations and variations may occur to those skilled in the art that are well within the scope of the inventive concept.

The present invention comprises a liquid humidity and oxygen control device comprising a polymeric film pouch having at least some walls sufficiently permeable to permit migration of water vapor and oxygen through the film and yet thick and impervious enough to prevent the escape of liquids. The control device may be used to control humidity and oxygen within a generally closed environment including but not limited to, an enclosure such as a container with a removable cap such as a glass jar for protecting the contents stored therein. The control device may be incorporated into the removable lid in certain embodiments or may be provided in addition to the removable lid. Certain embodiments comprise the control device being sealed against the upper surface of a glass jar by a removable cap. Alternatively, a control pouch comprising the aqueous humidity and oxygen control solution may be placed within the container.

A headspace may exist within the exemplary container, in addition to the contents within the container that require humidity and oxygen control.

Certain preferred embodiments may employ an aqueous humidity control solution including sodium formate, potassium citrate, potassium chloride or sodium chloride with or without a thickening agent such as xanthan gum.

Chemically reactive ascorbate and erythorbate salts may be included in the solution to eliminate oxygen which diffuses from the headspace, through the semi-permeable film to the liquid contents.

Very fine particles of iron may be added to the solution to enhance the oxygen reactivity. It was discovered that without the presence of the ascorbate isomers, the iron in this liquid oxidizes at a very slow rate. The solutions may contain excess solute to increase the capacity of the device to remove water vapor from the surroundings.

The polymeric film pouch may be constructed of any size or shape necessary to hold the amount of solution necessary to stabilize the humidity and oxygen of the environment, e.g., a container such as a glass jar with closed lid. For example, a typical device to maintain the humidity and oxygen level in a pint jar containing 10 grams of cannabis may comprise a pillow-like, water vapor and oxygen-permeable pouch containing about 8 grams of control solution.

The pouch of the present invention may be constructed of any polymeric material that contains the solution, but has a sufficient water vapor transmission rate and a sufficient oxygen transmission rate. A preferred packaging material comprises a thermoplastic polyester elastomer sold under the trademark Hytrel®. The polymeric material of the pouch may be selected from the group consisting of polyesters, polyamides, poly lactate, polyolefin, and combinations thereof.

The preferred range of water vapor transmission rate for the pouch material is one that transmits moisture from about 1 percent to about 40 percent by weight of the initial total package contents over a 24-hour period in an atmosphere of less than 10% relative humidity and wherein the pouch absorbs moisture from about 1 percent to about 40 percent by weight of total initial package contents over a 24-hour period in an atmosphere greater than 85 percent relative humidity.

The skilled artisan will now readily recognize moisture transmission and absorption preferred ranges, each of which are based on a reference temporal value of 24 hours combined with, in the case of transmission, an atmosphere of less than 10% relative humidity and, in the case of absorption, an atmosphere greater than 85% relative humidity. Thus, it will be appreciated that if the temporal value and and/or relative humidity value are changed from those stated reference values, the transmission and/or absorption values, respectively, will also change accordingly. Each of these transmission and absorption values are within the scope of the present invention so long as the preferred transmission and absorption values, as described above, at the reference temporal and relative humidity values, is satisfied.

In addition to the moisture transfer capability, the packaging film must transmit oxygen at a sufficient rate. The preferred range of oxygen permeability of the pouch material is such that it will transfer or transmit therethrough a minimum of 0.2 ml of headspace oxygen per square inch per 24-hour period at 70 degrees F. and atmospheric pressure.

The skilled artisan will now readily recognize that the preferred oxygen permeability is provided at given reference temperature and atmospheric pressure values and that, if the temperature and and/or atmospheric pressure values are changed from those reference values, the oxygen permeability will also change accordingly. Each of these oxygen permeability values are within the scope of the present invention so long as the preferred oxygen permeability, as described above, at the reference temperature and atmospheric pressure values is satisfied.

The preferred water vapor and oxygen permeable pouch materials include pouches comprising polymeric materials such as polyester, Hytrel®, or polyether block amide Pebax® that transmits water vapor, but not liquid water. Any material that meets the basic criteria might be used. Any receptacle that transmits water vapor and oxygen as desired and provides a barrier to liquids can be used. In addition, the moisture control system, sealed pouch may be contained in a second (outer) water vapor permeable pouch, bag or other container in order to provide back-up protection if the primary pouch should leak. Some, or all, of the control device pouch may be comprised of the water vapor and oxygen permeable materials described herein.

The solutions disclosed in this invention may contain from 15% to 75% water depending on the humidity of the environment to be controlled. The sodium formate, sodium chloride and potassium citrate are used to obtain the optimal humidity control, and certain formulations may contain an excess of these components, generally as crystals. Although thickening agents are not required or instrumental in controlling humidity, the humidity control solutions may be thickened to improve processing and minimize potential leaks. Although different thickeners can potentially be employed, brine tolerant xanthan gum (Danisco® SM) is preferred. The xanthan gum may be used at levels ranging from 0.1% to 0.7% to achieve the desired viscosity which is in the range of about 500 to about 7000 centipoise. In addition, the pouch device may comprise a vapor-permeable outer pouch for containing said pouch as a further protection against leaks.

The pH of the solution may be adjusted using common acids or bases such as, but not limited to, citric acid, lactic acid, formic acid, phosphoric acid, phosphate salts, sodium hydroxide, or potassium hydroxide. A preferred pH range is from about 6.0 to about 10.0. Ascorbic acid, erythorbic acid and their salts are preferred. Very small particles of iron are preferred due to the increased surface area and thus chemical reactivity.

A particular embodiment of the inventive salt solution within the inventive humidity and oxygen permeable pouch may comprise:

a saturated aqueous salt solution, salts of ascorbate isomers containing an amount of a salt solution from about 5% to 70% salt, and ascorbic acid salts, or isomers thereof, from 5 to 60%.

In addition, wherein the exemplary salt solution may comprise cations and anions, wherein the cations are selected from the group consisting of: lithium, sodium, potassium, calcium, and magnesium, and the anions are selected from the group consisting of: chloride, formate, acetate, phosphate, sulfate, citrate, lactate, malate and tartrate.

The exemplary salt solution may further comprise nonionic substances selected from the group consisting of: propylene glycol, glycerin, and at least one simple sugar, wherein the at least one simple sugar is selected from the group consisting of: glucose and fructose and sugar alcohols, and wherein the sugar alcohol is selected from the group consisting of: xylitol, sorbitol and mannitol.

The exemplary salt solution may comprise a pH that is between 6.0 and 10, wherein the pH of the exemplary salt solution may be adjusted by adding an amount of an acid or base selected from the group consisting of citric acid, lactic acid, formic acid, phosphoric acid, phosphate salts, sodium hydroxide, and potassium hydroxide.

The exemplary salt solution may contain ascorbate isomer salts and/or erythorbic isomer salts, wherein the ascorbate isomer salts comprise sodium salts of ascorbic acid and/or potassium salts of ascorbic acid, and wherein the erythorbic isomer salts comprise sodium salts of erythorbic acid and/or potassium salts of erythorbic acid and, in some embodiments, at least one metal. In some embodiments, the at least one metal comprises iron including elemental iron.

The exemplary salt solution may contain a ferrous salt, e.g., ferrous sulfate.

The exemplary salt solution may be thickened by an amount of one or more compatible viscosity control agents selected from the group consisting of chemically modified cellulose and xanthan gum.

Operation

In use, the humidity and oxygen control devices of the present invention are placed in a sealed enclosure containing the material to be protected by oxygen elimination and controlled humidity. For example, one or more pouches may be placed in a jar or plastic container enclosure with cannabis. Theoretically, if the pouch is sized correctly and the product container enclosure has a perfect seal, oxygen would be eliminated and the controlled humidity would be maintained indefinitely. However, actual environments are less than ideal and containers tend to leak and may be opened and closed from time to time. Accordingly, a given pouch of the present invention will gain water or lose water in such a fashion as to protect the contents until the pouch has gained or lost water exceeding its moisture transfer capacity. Headspace oxygen will diffuse into the pouch and be consumed by the ascorbate or erythorbate salts until they are totally oxidized or all of the headspace oxygen is consumed.

FIGS. 1 and 2 illustrate one example of the present invention. FIG. 1 illustrates one embodiment of a control pouch 10 comprising a generally circular backing 12 that is neither water nor oxygen permeable and with a water and oxygen permeable pouch 14 attached thereto. The inventive aqueous solution as described herein is provided within permeable pouch 14. A circular portion 16 of the circular backing 12 is left uncovered. The circular portion 16 is sized to engage a top surface 18 of the exemplary glass jar container 20. Glass jar 20 further comprises threads 22 and an interior volume 24. A threaded lid 26 is also provided to seal the control pouch 10 such that the circular portion 16 of the circular backing is engaging the top surface 18 of glass jar container 20 and wherein the exemplary pouch 14 is disposed within the interior volume 24 of the glass jar container 20. The contents to be protected (not shown) are placed within the interior volume 24 prior to sealing the container. The portion of the interior volume 24 that is not occupied by the contents to be protected therein comprises the headspace as is well known to the skilled artisan. The impermeable circular backing material 12 prevents water vapor or oxygen from entering or exiting the interior volume 24 once the container is sealed.

Circular portion 16 may, in certain embodiments, comprise an adhesive material to assist in securing the control pouch 10 to the top surface 18 of glass jar container 20. As will be appreciated, the circular backing 12 may be sized to accommodate various sizes of glass jar containers, specifically circular backing 12 may comprise a diameter that matches the diameter of the top surface 18 of glass jar container 20.

In other embodiments, control pouch 10 may be simply placed within a container. Some of these embodiments need not necessarily comprise circular backing 12.

WORKING EXAMPLES

Example 1A

In one embodiment of the present invention, an aqueous solution of potassium chloride and sodium erythrobate is prepared by adding 20.9 grams of potassium chloride, 16.7 grams of erythorbic acid, and 0.2 grams of potassium sorbate to 55 grams of water. Potassium hydroxide (7.2 grams) is carefully added to this mixture. The pH of this solution is 8.0 and the relative humidity 82% (water activity 0.82). Eight grams of this solution was filled into a pouch comprised of Hytrel® film (DuPont) (1.5×10−3 inches thick) on a paper substrate. The pouch measures 2.5 inches by 2.75 inches with a 5 mm heat seal on three sides. When placed in a dry atmosphere (10% RH), this device emitted 40% of the solution weight as moisture before it reached 80% RH (aw 0.80).

When this device was placed in a 240 ml metalized package at 70 degrees F. with air headspace, a pouch containing 8.0 grams of the above solution consumed 38 ml of oxygen in 19 days.

Example 1B

Example 1 was repeated with the addition of 0.8 grams of 500 mesh iron added to the 8.0 gram Hytrel® pouch. When placed in a 240 ml metalized package at 70 degrees F. with air headspace, this pouch consumed 50 ml of oxygen in 19 days.

Example 2A

In another embodiment of the present invention, an aqueous solution of potassium citrate and potassium erythorbate was prepared by adding 58.0 grams of potassium citrate monohydrate, 10.0 grams of erythorbic acid, 3.3 grams of potassium hydroxide and 0.2 grams of xanthan gum to 28.5 grams of water. The pH of the solution was 7.6 and the water activity 0.60 (RH 60%). Eight grams of this solution was filled into a Hytrel® pouch as described in Example 1A. When placed in a dry atmosphere, this device emitted 20% moisture to a water activity of 0.55 (55% RH). In a high humidity environment (85% RH), this device gained 10% moisture before reaching 69% RH (aw 0.69).

When this device was placed in a 240 ml metalized package at 70 degrees F. with air headspace, a pouch containing 8.0 grams of this solution consumed 26 ml of oxygen in 7 weeks.

Example 2B

Example 2 was repeated with the addition of 0.4 grams of 500 mesh iron added to the 8.0 gram Hytrel® pouch. When placed in a 240 ml metalized package at 70 degrees F. with air headspace, this pouch consumed 32 ml of oxygen in 7 weeks.

Example 3A

In another embodiment of the present invention, an aqueous solution of sodium formate and sodium ascorbate was prepared by adding 43.0 grams of sodium formate and 14.0 grams sodium ascorbate to 43.0 grams of water. The pH of this solution was 8.0 and the water activity 0.55 (RH 55%). Eight grams of this solution was filled into a pouch comprised of Hytrel® film as in Example 1A. When placed in a dry atmosphere (10% RH), this devise emitted 38% water vapor while maintaining a water activity between 0.55 (55% RH) and 0.52 (52% RH). When placed in a high humidity environment (84% RH) the pouch gained 30% moisture before reaching a water activity of 0.68 (68% RH).

When placed in a 240 ml metalized package at 70 degrees F. with air headspace, a pouch containing 8.0 grams of this solution consumed 29 ml of oxygen in 20 days.

Example 3B

Example 3 was repeated with the addition of 0.4 grams of 500 mesh iron added to the 8.0 gram Hytrel® pouch. When placed in a 240 ml metalized package at 70 degrees F. with air headspace, this pouch consumed 46 ml of oxygen in 20 days.

Example 4A

A solution of sodium ascorbate was prepared by adding 30 grams of sodium ascorbate, 0.1 grains of potassium sorbate to 30 grams of water. The pH of this solution was 7.6 and the water activity 0.85 (85% RH). Eight grams of this solution was placed in a Hytrel® pouch as in Example 1A. When placed in a dry atmosphere (10% RH), this devise emitted 42% water vapor while maintaining a water activity between 0.85 (85% RH) and 0.83 (83% RH).

When placed in a 240 ml metalized package at 70 degrees F. with air headspace, a pouch containing 8.0 grams of this solution consumed 34 ml of oxygen in 20 days. The pH decreased to 6.1.

Example 4B

Example 4 was repeated with the addition of 0.4 grams of 500 mesh iron added to the 8.0 gram Hytrel® pouch. When placed in a 240 ml metalized package at 70 degrees F. with air headspace, this pouch consumed 43 ml of oxygen in 20 days. The pH decreased to 6.8.

The descriptions of the embodiments and their applications as set forth herein should be construed as illustrative, and are not intended to limit the scope of the disclosure. Features of various embodiments may be combined with other embodiments and/or features thereof within the metes and bounds of the disclosure. Upon study of this disclosure, variations and modifications of the embodiments disclosed herein are possible, and practical alternatives to and equivalents of the various elements of the embodiments will be understood by and become apparent to those of ordinary skill in the art. Such variations and modifications of the embodiments disclosed herein may be made without departing from the scope and spirit of the invention. Therefore, all alternatives, variations, modifications, etc., as may become to one of ordinary skill in the art are considered as being within the metes and bounds of the instant disclosure.

What is claimed is:

1. A liquid humidity and oxygen control device for use in an enclosure for maintaining a desired relative humidity and oxygen level of the enclosure, the device comprising:

a water vapor and oxygen permeable and liquid impermeable pouch, the pouch defining an interior space, and formed from material comprising an oxygen permeability rate comprising, in an atmosphere of approximately 70 degrees F., at least 0.2 ml of headspace oxygen per square inch per 24-hour period; and an effective amount of a humidity and oxygen control solution disposed within the interior space and comprising a salt solution comprising a nonionic substance selected from the group consisting of propylene glycol, glycerin, and a simple sugar.

2. The humidity and oxygen control device of claim 1, wherein the at least one simple sugar is selected from the group consisting of: glucose, and fructose and sugar alcohols.

3. The humidity and oxygen control device of claim 2, wherein the sugar alcohol is selected from the group consisting of: xylitol, sorbitol and mannitol.

4. The humidity and oxygen control device of claim 1, wherein the pH of the solution is between 6.0 and 10.

5. The humidity and oxygen control device of claim 1, where the solution contains at least one of ascorbate isomer salts and erythorbic isomer salts.

6. The humidity and oxygen control device of claim 1, wherein said humidity control solution is thickened by an amount of one or more compatible viscosity control agents selected from the group consisting of chemically modified cellulose and xanthan gum.

7. The humidity and oxygen control device of claim 1, wherein material of the pouch is selected from the group consisting of polyesters, polyamides, poly lactate, polyolefin, and combinations thereof.

8. The humidity and oxygen control device of claim 1, further comprising a water vapor and oxygen impermeable backing configured to be arranged over an opening of the enclosure.

9. The humidity and oxygen control device of claim 8, wherein the backing comprises an adhesive material.

10. A non-plastic container defining a volume therein, the container having a lid configured to enclose an opening of the container, and comprising:
a humidity and oxygen control device for maintaining a desired relative humidity and oxygen level within the container, the humidity and oxygen control device comprising:
a water vapor and oxygen permeable and liquid impermeable pouch arranged within the container, the pouch defining an interior space, and formed from material comprising an oxygen permeability rate; and
an effective amount of a humidity and oxygen control material disposed within the interior space of the pouch and comprising a salt solution comprising a nonionic substance selected from the group consisting of propylene glycol, glycerin, and a simple sugar.

11. The container of claim 10, wherein the oxygen permeability rate comprises, in an atmosphere of approximately 70 degrees F., at least 0.2 ml of headspace oxygen per square inch per 24-hour period.

12. The container of claim 10, wherein the lid comprises threading for engaging threading of the container.

13. The container of claim 10, wherein the humidity and oxygen control device comprises a water vapor and oxygen impermeable backing configured to be arranged between the lid and the opening of the container.

14. The container of claim 13, wherein the backing comprises an adhesive material.

15. The container of claim 10, wherein the at least one simple sugar is selected from the group consisting of: glucose, fructose, and sugar alcohols.

16. The container of claim 15, wherein the sugar alcohol is selected from the group consisting of: xylitol, sorbitol and mannitol.

17. A lid for an enclosure of an opening of a non-plastic container defining a volume therein, the lid comprising:
a container engaging portion; and
a humidity and oxygen control device for maintaining a desired relative humidity and oxygen level within the container, the humidity and oxygen control device comprising:
a humidity and oxygen impermeable backing configured to be arranged between the container engaging portion and an opening of the container;
coupled to the backing, a water vapor and oxygen permeable and liquid impermeable pouch configured to be arranged within the container, the pouch defining an interior space, and formed from material comprising an oxygen permeability rate; and
an effective amount of a humidity and oxygen control material disposed within the interior space of the pouch and comprising a salt solution comprising a nonionic substance selected from the group consisting of propylene glycol, glycerin, and a simple sugar.

18. The lid of claim 17, wherein the oxygen permeability rate comprises, in an atmosphere of approximately 70 degrees F., at least 0.2 ml of headspace oxygen per square inch per 24-hour period.

19. The lid of claim 17, wherein the container engaging portion comprises threading for engaging threading of the container.

20. The lid of claim 17, wherein the backing comprises an adhesive material.

* * * * *